United States Patent
Brown et al.

(10) Patent No.: US 9,204,984 B2
(45) Date of Patent: Dec. 8, 2015

(54) CONTOUR BRACING

(71) Applicant: Azimuth Technical Consultants, Inc., Sugarloaf Key, FL (US)

(72) Inventors: Robert Brown, Sugarloaf Key, FL (US); Mario Santos, Sugarloaf Key, FL (US)

(73) Assignee: Azimuth Technical Consultants, Inc., Sugarloaf Key, FL (US)

( * ) Notice: Subject to any disclaimer, the term of this patent is extended or adjusted under 35 U.S.C. 154(b) by 19 days.

(21) Appl. No.: 13/907,210

(22) Filed: May 31, 2013

(65) Prior Publication Data

US 2014/0012171 A1    Jan. 9, 2014

Related U.S. Application Data

(60) Provisional application No. 61/653,547, filed on May 31, 2012.

(51) Int. Cl.
| | |
|---|---|
| *A61F 5/00* | (2006.01) |
| *A61F 5/02* | (2006.01) |
| *A61F 5/01* | (2006.01) |
| *A61F 5/04* | (2006.01) |
| *A61F 5/05* | (2006.01) |
| *A61F 5/058* | (2006.01) |
| *A61F 5/042* | (2006.01) |

(52) U.S. Cl.
CPC . *A61F 5/01* (2013.01); *A61F 5/012* (2013.01); *A61F 5/0106* (2013.01); *A61F 5/02* (2013.01); *A61F 5/028* (2013.01); *A61F 5/04* (2013.01); *A61F 5/05* (2013.01); *A61F 5/058* (2013.01); *A61F 5/05816* (2013.01); *A61F 5/042* (2013.01)

(58) Field of Classification Search
CPC .............. A61F 5/00; A61F 5/012; A61F 5/02; A61F 5/022; A61F 5/024; A61F 5/026; A61F 5/028; A61F 5/04; A61F 5/042; A61F 5/05; A61F 5/058; A61F 5/05816
USPC ............ 602/13, 19, 32, 36, 12; 128/869, 870, 128/874; 2/463, 464, 467, 44, 92, DIG. 3
See application file for complete search history.

(56) References Cited

U.S. PATENT DOCUMENTS

| | | | |
|---|---|---|---|
| 3,993,056 A * | 11/1976 | Rabischong et al. | 602/13 |
| 5,867,842 A * | 2/1999 | Pinsley et al. | 2/462 |
| 6,237,602 B1 * | 5/2001 | Nickels et al. | 128/874 |
| 7,771,376 B2 * | 8/2010 | Roth et al. | 601/152 |
| 7,938,486 B2 | 5/2011 | Porat et al. | |

(Continued)

OTHER PUBLICATIONS

DDS 300 Back Brace, How the DDS 300 Back Brace Works, "DDS 300: How it Works", http://www.worldsbestbackbrace.com/how-it-works/, 7 pages (downloaded May 11, 2015).

(Continued)

*Primary Examiner* — Alireza Nia
*Assistant Examiner* — Keri J Nelson
(74) *Attorney, Agent, or Firm* — Fish & Richardson P.C.

(57) ABSTRACT

A wearable brace includes: elongated structural members disposed substantially in parallel with each other, each structural member engaged with at least one adjacent structural member; and an inflatable member disposed between two adjacent structural members such that inflation of the inflatable member biases portions of the two adjacent structural members away from each other.

18 Claims, 7 Drawing Sheets

(56) References Cited

U.S. PATENT DOCUMENTS

2004/0239161 A1    12/2004   Lee
2008/0197688 A1    8/2008   Tate

OTHER PUBLICATIONS

Decompression Back Belt, 2-in-1 Decompression Back Belt with FREE Magic Heat Pad, http://www.drhonow.com/product/decompression-belt-how-it-works.php, 2011, 6 pages (downloaded May 11, 2015).

Malanga et al., "Low Back Pain Relief and Pneumatic Vest Use", http://www.spineuniverse.com/exams-tests/devices/low-back-pain-relief-pneumaticvest-use, 2 pages (downloaded May 11, 2015).

Form Fit Advanced Back Support, http://www.assets.ossur.com/library/15874/OrthoCatalog09%2077.pdf, 1 page (downloaded May 11, 2015).

* cited by examiner

CONTOUR BRACING

CROSS-REFERENCE TO RELATED APPLICATION

This application is a non-provisional of U.S. Application Ser. No. 61/653,547 filed May 31, 2012, the entire content of which is incorporated herein by reference.

TECHNICAL FIELD

This invention relates to bracing body joints, and more particularly to bracing body joints with a specific contoured shape to provide incremental lift or compression, alignment, and support.

BACKGROUND

Back pain can be caused by compression. Gravity is constantly acting on the body and over time slowly forces the spine closer together. This is one of the reasons why elderly people appear to shrink with age—where their spines are actually compressing. Additionally, back pain is common amongst office workers that spend a majority of time at their desk/chair sitting. Improper posture and slouching coupled with hours of inactivity can result in chronic back pain.

The lumbar region (or lower back region) is made up of five vertebrae (L1-L5). In between these vertebrae lie fibrocartilage discs (intervertebral discs), which act as cushions, preventing the vertebrae from rubbing together while at the same time protecting the spinal cord. Nerves stem from the spinal cord extend through forming within the vertebrae, providing muscles with sensations and motor-associated messages. Stability of the spine is provided through ligaments and muscles of the back, lower back and abdomen. Small joints which prevent, as well as direct, motion of the spine are called facet joints (zygapophysial joints).

Causes of lower back pain can be varied. In some cases, it can be due to a sprain or strain in the muscles and soft tissues of the back. Over use of the muscles of the back can lead to an injured or torn ligament in the back which in turn leads to pain. An injury can also occur to one of the intervertebral discs (disc tear, disc herniation). Due to aging, discs begin to reduce in size, resulting in vertebrae and facet joints rubbing against one another. Ligament and joint functionality also diminishes as aging progresses, leading to spondylolisthesis, which causes the vertebrae to move more than they should. Pain is also generated through lumbar spinal stenosis, sciatica and scoliosis. At the lowest end of the spine, pain can be experienced at the tailbone (also called coccyx pain or coccydynia). Pain can also result at the sacroiliac joint, where the spinal column attaches to the pelvis, called sacroiliac joint dysfunction. Physical causes may include osteoarthritis, rheumatoid arthritis, degeneration of the discs between the vertebrae or a spinal disc herniation, a vertebral fracture (such as from osteoporosis).

Spinal manipulation is a therapeutic intervention that has roots in traditional medicine and has been used by various cultures, apparently for thousands of years. Hippocrates, the "father of medicine" used manipulative techniques, as did the ancient Egyptians and many other cultures. A modern re-emphasis on manipulative therapy occurred in the late 19th century in North America with the emergence of osteopathic medicine and chiropractic. Spinal manipulative therapy gained recognition by mainstream medicine during the 1980s.

It is not known if chiropractic care improves clinical outcomes in those with lower back pain more or less than other possible treatments. A 2004 Cochrane review found that spinal manipulation (SM) was no more or less effective than other commonly used therapies such as pain medication, physical therapy, exercises, back school or the care given by a general practitioner. A 2010 systematic review found that most studies suggest SM achieves equal or superior improvement in pain relief and function when compared with other commonly used interventions for short, intermediate, and long-term follow-up. In 2007, the American College of Physicians and the American Pain Society jointly recommended that clinicians consider spinal manipulation for patients who do not improve with aforementioned options. Reviews published in 2008 and 2006 suggested that SM for lower back pain was equally effective as other commonly used interventions.

Over a lifetime, 80% of people have lower back pain, with 26% of American adults reporting pain of at least one day in duration every three months. 41% of adults aged between 26 and 44 years reported having back pain in the previous 6 months. In the United States, the costs of low back pain range between $38 and $50 billion a year and there are 300,000 operations annually. Along with neck operations, back operations are the 3rd most common form of surgery in the United States.

SUMMARY

This disclosure relates to bracing body joints, and more particularly to bracing body joints with a specific contoured shape to provide incremental lift or compression, alignment, and support via a "stacked" fluid-actuated brace system. This system utilizes a stacked interlocking design of molded/shaped flexible material (e.g., urethane, silicone, rubber, etc.) and internal inflatable tubes to provide the lift, alignment, and support in response to a result of injury, post-surgery or general ambulatory needs. Additionally, the brace can be used by athletes to limit the joint contact/impact (e.g., in knees) or used in a compressive mode for people with anterior cruciate ligament (ACL) conditions. This system is semi-passive and low profile and can be fabricated with or without the metal supports or hinges typically found in other systems. The outer and inner lining material can consist of a layer of flexible material with a high coefficient of friction (wet) with the body skin to provide the grip needed to maintain brace/skin contact continuity to help prevent brace sliding. Some embodiments are implemented with 2-8 mil's of elastic fabric with slip resistant silicone or similar material on the inside. The thickness of the lining material varies with application.

The stacked interlocking rib members/tubes are reinforced and joined/interlocked with, for example, molded urethane, solid rubber, or other materials that can be alternated and reversed for directional force on each side of the specific body joint or for lumbar support.

In one aspect, a wearable brace includes: a plurality of elongated structural members disposed substantially in parallel with each other, each structural member engaged with at least one adjacent structural member; and at least one inflatable member disposed between two adjacent structural members such that inflation of the inflatable member biases portions of the two adjacent structural members away from each other. Embodiments can include one or more following features. Some embodiments include combinations of all following features.

In some embodiments, wherein each of the structural members has a male end and a female end sized such that the male end of one of the structural members can be inserted in slideable engagement into the female end of an adjacent structural member. In some cases, the male end of each of the structural members comprises radially extending features that limit movement of two adjacent structural members away from each other after the male end of one of the structural members is inserted in slideable engagement into the female end of the adjacent structural member.

In some embodiments, the at least one inflatable member comprises one inflatable member disposed extending in a serpentine fashion between multiple sets of two adjacent structural members such that inflation of the one inflatable member biases portions of the two adjacent structural members in each set of two adjacent structural members away from each other.

In some embodiments, the at least one inflatable member comprises multiple inflatable members, each of the multiple inflatable members disposed between a different two adjacent structural members. In some cases, each of the multiple inflatable members are fluidly connected to at least one other of the multiple inflatable members such the fluid used to fill the inflatable members extends in a serpentine fashion between multiple sets of two adjacent structural members. In some cases, prices also include a manifold connected to each of the multiple inflatable members.

In some embodiments, braces also include a cover with the plurality of elongated structural members and the at least one inflatable member substantially disposed within the cover. In some cases, the cover is configured to be worn on a torso of a user. The plurality of elongated structural members and the at least one inflatable member can be sized to extend from hips of the user to armpits of the user.

In some embodiments, the cover is configured to be worn on a limb of a user. In some cases, the cover is configured to be worn on a limb of a user. The cover can be configured to be worn on a leg of a user.

In some embodiments, braces also include a retraction mechanism biasing the plurality of elongated structural members towards a retracted position, the refraction mechanism configured to elastically expand when the plurality of elongated structural members are in an extended position. In some cases, the retraction mechanism comprises an elastic band extending around multiple elongated structural members of the plurality of elongated structural members towards a retracted position. In some cases, the retraction mechanism comprises a cover made of an elastic fabric with the plurality of elongated structural members and the at least one inflatable member substantially disposed within the cover.

In some embodiments, a garment includes: a plurality of elongated structural members disposed substantially in parallel with each other, each structural member engaged with at least one adjacent structural member, wherein each of the structural members has a male end and a female end sized such that the male end of one of the structural members can be inserted in slidable engagement into the female end of an adjacent structural member; at least one inflatable member disposed between two adjacent structural members such that inflation of the inflatable member biases portions of the two adjacent structural members away from each other; and a cover with the plurality of elongated structural members and the at least one inflatable member substantially disposed within the cover. In some cases, the at least one inflatable member comprises multiple inflatable members, each of the multiple inflatable members disposed between a different two adjacent structural members. In some cases, garments also include a manifold connected to each of the multiple inflatable members. In some cases, garments also include a retraction mechanism biasing the plurality of elongated structural members towards a retracted position, the refraction mechanism configured to elastically expand when the plurality of elongated structural members are in an extended position.

The brace (when used for the back) is designed to relieve the pressure on spinal components so that the discs between the vertebras are relieved of compressive force.

The brace helps mitigate musculoskeletal problems associated with spinal compression and improper posture.

The concept behind the brace for Back Mobilization Therapy or "Spinal Manipulation" centers on the principle of positioning the body so that the spinal compression is placed into spinal tension "while upright", This helps relieve pressure on spinal discs and nerves by lifting and stretching the entire back as compared to products that push/compress the lower part of the upper torso upward. As the upper torso is suspended in traction, the brace reduces the pressure placed on the spinal discs and nerves and stretches the back muscles.

The device can be integrated into a garment/vest, with adaptations for other joint related needs. The invention for the back is designed to relieve the pressure on spinal components (muscles, rhomboid, thoracolumbar, erector spinae, etc. and associated nerves) so that the discs between the vertebras are relieved of compressive force.

The brace system can be used as a garment around the chest (either exterior vest or undergarment) that mechanically lifts the upper torso from the hips (or foundation) causing a separation between the discs of the spine while stretching the muscles in the back. This device uses multiple/individually stacked and interlocking housing system for internal tubes to provide distributed and targeted upper torso separation while also enhancing proper posture that can integrate an inflatable lumbar support system. This portable device can be utilized for ambulatory purposes, therapy, ergonomic support while in a chair (office or airline seating), or prolonged standing (assembly line); or by athletes for sports such as, for example, jogging, football (also serve as impact protection), skiing, soccer, etc.

Other embodiments of the brace system apply a supporting and suspending force around the upper torso that allows the weight of the upper part of the lower torso to stretch the muscles and allow the spine to settle while in the upright or sitting position. This device applies a spinal manipulation that allows pain relief of the lower and upper back. The device manipulates the lower spine by providing a firm support to the upper thoracic spine and transfers a significant amount of the load on the lower spine to the support mechanism and hips. This allows the lower spine to be relaxed so that the vertebra can separate and be restored to a more normal condition. This relief of the upper body weight on the lower spine is an important aspect of the design when compared to other lower back supports that push or compress the lower spine upward against the upper torso.

When used as a garment, the contour brace for back mobilization can offer support to the entire back as an ergonomic device while the individual is exerting force (e.g., resulting from lifting or general labor that stresses the back muscles and nerves). Back pain experienced in a vehicle (e.g., aircraft or automobile seating) is another application where the contour brace can be passively worn in contrast to other device that rely on active traction to provide back support in a decompressed mode to the spine and muscles. Additionally, the contour brace has the adaptation capability to provide females lift to the breasts (as supported from the hips on up through the upper torso while providing back support).

The contour brace has a smaller profile and provides more equally distributed force distribution than braces that rely on piston or bladder lifting systems. For example, piston-lifting system braces concentrate/focus its lifting forces at the points around the lower portion of the upper torso where a limited number of pistons are located. The pistons create a point sourced loading at locations around the hips as well.

The combined rib members and inflatable tubes can enable the contour brace for back mobilization therapy to engage and lift throughout the entire vertical length and horizontal perimeter of the upper torso, spine, back/ribcage to the armpits and lower shoulder blades and contours around the upper torso for a uniform fit. This provides distributed lift of the upper torso while also decompressing the spine discs from L5-L1-TH4. Additional lift and support occurs throughout the length of the back muscles and can be either a telescoping lift or uniform lift throughout the entire back as controlled by the tube inflation within the rib/housing. This approach can provide therapeutic advantages relative to bladder or piston based systems which compress the upper spine at the upper thoratic curve and does not address upper back spinal, muscles or posture concerns above L5, limiting its overall and intended effectiveness.

The contour brace is unique in comparison to other systems as it addresses the entire back from the hips to the armpits and shoulder blades based on a uniform shape/fitting lifting system. This is achieved by the unique concept of the rib members and tube system that has the engineering capabilities to support a heavy upper torso. This is the primary technology difference between the contour brace and other back systems where the rib member and tubes are capable of supporting evenly distributed large loads (the upper torso can be ⅔ of the total body weight). No other back device offers a flexible shaped system capable of addressing the entire back with a robustly engineered lifting and supporting solution while in the "upright position". The contour brace achieves the spinal and muscular benefits of the inversion table without the fear of being turned upside down such as the inversion table. The inversion table duration can be limited for a very short time (a few minutes/day) due to blood flow to the head. Additionally, the inversion table can have potentially adverse effects to the joint/bone/ligament of the hips, knees and ankles (especially for an older person). Additionally, inversion tables present a serious danger to users that are at risk for high blood pressure, have other forms of heart disease or have bone fractures. As you invert your body, your heart rate slows down and your blood pressure begins to rise. Use of any medication or have any disease may cause a health risk while inverted.

Other implementations include embodiments adapted to provide support: to the neck as a neck brace and/or to adjust jaw alignment to control esophagus/air passage for sleep apnea or breathing disorder; to the knee; etc.

Implementations of the contour brace for back mobilization therapy can provide better biomechanics (both kinetics and kinematics) for spinal manipulation than manual therapy interventions such as chiropractic mobilization or inversion table use in that the therapy provided is ongoing rather than episodic.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

In one application, the brace can be configured as a back and posture device that uses a lifting and alignment system to therapeutically and incrementally provide relief to both the upper and lower back via spinal mobilization and kinematics in the upright, standing, sitting or reclining position. While the upper torso is supported/suspended by the lifting device, the weight and/or lift from the lower torso and hips provides the opposing force to help the spine manually settle and relax into the correct posture as directed by the contour brace system. This can be extremely beneficial for older users with sensitive bone and joint structure that cannot utilize inversion systems.

The integrated rib members and serpentine tube are located around the upper torso starting at the hips (like a belt) and following the ribcage. The inflation or pressurization of the tube can be directed upward and inward towards the body with lift taking place from the hips to underneath the armpits. The individual travel of each rib member and tube can be 0.25 inches-0.375 inches; with a cumulative upward lift distance based on the quantity of rib members and tube length chosen in part to account for mechanical losses in the system and torso stretch (skin travel). The interlocking rib member can be a flexible and grooved interlocking molded or extruded urethane (but not limited to urethane material) system that will provide support with motion flexibility.

Figure 1A:
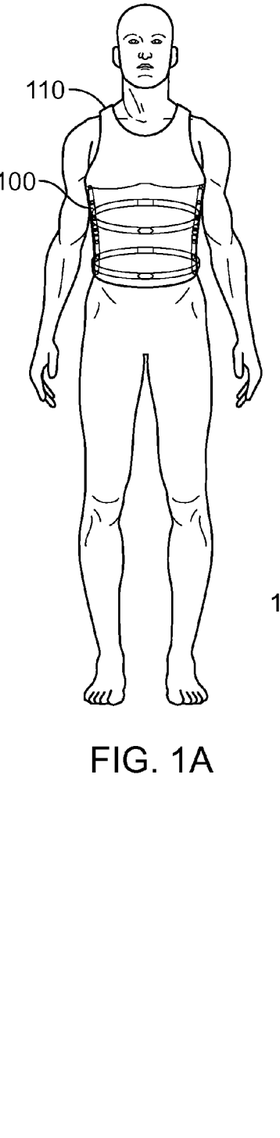
FIGS. 1A and 1B are schematic illustrations of a user wearing a contour back brace.
Figure 1B:
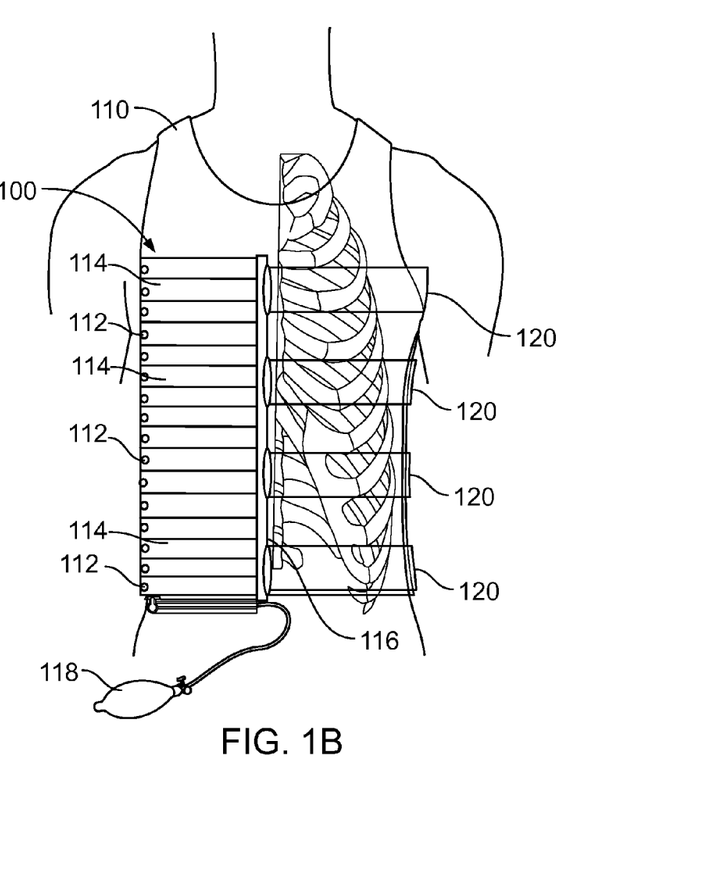

FIGS. 1A and 1B illustrate an exemplary brace 100 for back mobilization therapy that is configured as a portable and passive vest/undergarment 100. This device 100 provides distributed support and lift throughout the upper-torso/chest from the hips to the armpit. The principle is to provide a comfortable lift with evenly distributed forces via each rib member/inflatable tube over the entire chest/ribcage. These evenly distributed forces can provide a more comfortable lift than systems in which forces applied to the body at discrete concentrated locations. The brace 100 includes a fabric cover 110 containing a flexible support structure 111. The flexible support structure 111 includes inflatable tube/s 112 disposed within a series of interlocking rib members 114. "Tube/s" include, for example, elongated hollow structures without indicating a particular cross-sectional shape. The illustrated tube/s 112 have a circular cross-section but some tubes have different cross-sectional shapes. "Ribs" include, for example, elongated structures with a high length to height/width aspect ratio (e.g., 100:1, 75:1, 50:1, 40:1, 30:1, 20:1, 15:1, 10:1, etc.).

The illustrated brace 100 includes interlocking rib members 114 with inflatable tube/s 112. A manifold 116 connects the inflatable tubes 112. The manifold 116 includes a port through which fluid can be introduced into or release from the manifold 116 and the inflatable tubes 112. A detachable pump 118 with a quick disconnect coupling is operable to pump fluid into the manifold 116 and the inflatable tubes 112 to inflate the brace during use. Some braces incorporate other inflation mechanisms such as, for example, an internal pump, a pressurized gas cylinder, etc. Use of a detachable pump allows multiple braces to be inflated by a single pump and reduces the weight of the brace during use. Use of an integral pump means that an inflation mechanism is available if, for example, a brace needs to be re-inflated during use.

The detachable pump 118 is a pneumatic pump used to inflate the brace 100 with air. However, some embodiments of this brace are designed to be filled with other fluids (e.g., water, gel, etc) and these braces are filled using pumps or inflation mechanisms appropriate for the fluids. For example, thermal therapy can be applied in conjunction with body support by using heated or chilled water to inflate the brace 100. However, an air-filled brace 100 will be lighter than a water-filled brace 100.

Figure 6:
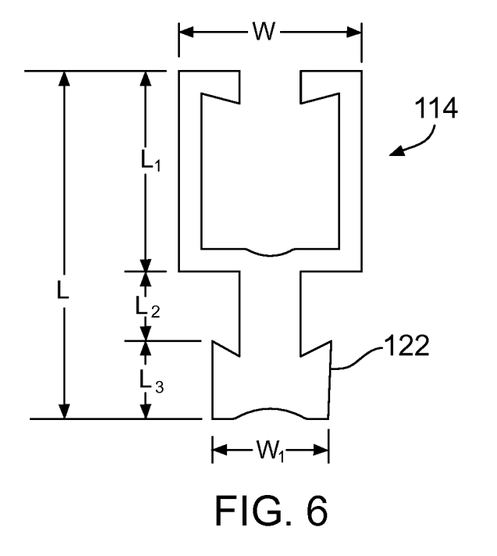
FIG. 6 is a cross-section of an individual rib member.

The illustrated brace 100 includes 5 interlocking rib members 114 with 5 inflatable tubes 112. However, the size of the brace and the number of sets of inflatable tubes 112 and rib members 114 can be varied to fit individuals with different sized frames. The braces 100 can be manufactured with more sets (e.g., 6, 7, 8, 9, 10, 12, 14, 16, 18, 20, etc.) sets of rib members 114 and inflatable tubes 112 (or a singular serpentine tube). For example, FIG. 6 shows the inner components of a brace including 16 sets of inflatable tubes 112 and rib members 114. The brace 100 can be distributed preassembled in different sizes (e.g., small, medium, large, etc.). However, the modular nature of the braces also support adding or removing sets of rib members 114 and inflatable tubes 112 (or singular) to adjust the size of a specific brace for a specific user.

The brace 100 includes four straps 120 to secure the brace around the user's torso, for example, before inflation. Other embodiments are implemented with different numbers of securing straps. The straps (e.g., Velcro hook and loop fastener straps) are attached to the front of the harness to cinch up the complete contour brace system around the waist, midsection, and lower portion of the upper torso prior to inflation. These straps can be located so they are directly pulling on the rib member portion of the vest either over the tubes or directly on the rib member. Zipper systems can also be incorporated into the brace to provide a secure fit as an additional embodiment.

The rib member/tube/s lifting system is encapsulated in a stretchable garment such as, for example, neoprene, cotton stretch denim, Cordura or TEMBO® Elastic Memory Composites (EMC) that combines the structural properties of fiber reinforced composites with shape memory characteristics of shape memory polymers. Components and structures fabricated with TEMBO® EMC materials can provide lightweight structures that are strong and stiff) to allow for the expansion or growth of the rib member/tubes. The stitching of this elastic fabric combined with vertical supports (i.e. boning, composites/platics) spaced perpendicular to the rib members (around the perimeter and on both outside and inside of the rib members) provides additional brace system support and contour shaping. Also, on the inside of the contour brace, a flexible/semi-adhesive material (e.g., silicone rubber, Neoprene, gum rubber, etc.) or directional adhesive microfibers made from a hard polymer, polypropylene will be utilized. In one embodiment, the polymer fibers are 600 nanometers in diameter, just 1/100 the diameter of a human hair, and are formed by a casting process. The synthetic microfiber array is not sticky except when fibers slide a small distance along a surface. These materials are intended to provide a high coefficient of friction against the upper torso for good "grip".

FIGS. 2A-2E illustrates the inner components of a brace with 5 sets of rib members 114 and inflatable tubes 112. Each rib member 114 has a male end 122 and a female end 124. The interlocking male 122 and female 124 ends include complementary notched features (best seen in FIG. 2D) to prevent the "pull out" of the rib member from one another during expansion from pressurization of the tubes. The rib members house the inflatable tubes that apply the lift while the rib members control/limit the lift height. Prototype rib members manufactured from a urethane material of approximately 65 durometer. Rib members can also be made of other flexible material (e.g., silicone, rubber, etc.) and/or with other durometer set points depending, for example, on intended location of brace on body and the type of joint application. Tubes in a prototype were formed of a 6088 white PVC material 0.180 inch outer diameter tube with a 0.017 wall thickness capable of containing pressures in excess of 50 psig. Other inflatable material can also be used to form the tubes. For example, rubber tubing can also be used. However, one singular serpentine tube can be used to improve quality and mitigate the potential for joint leaks.

The system can be aligned with the static points aligned with different locations on the body to control where traction/compression/support is applied. The rib members can be arranged via the interlocking system at various locations/heights on the contour brace to maximize lift and adapt to the individuals shape and size.

The specialized tube system that is internal to the rib member and can serpentine as one continuous system or connected to a manifold for unified inflation via a fluid (e.g., pneumatic or liquid), with an in-situ or detachable (e.g., quick disconnect) hand pump. A single point inflation or manifold system can be integrated with the contour brace to provide the inflation/pressurization to the tubes via a quick disconnect pump 118 (e.g., a manual pump, an electric pump, etc.). In the brace 100, the individual inflatable tubes 112 are placed within the female end 124 of each rib member and connected using barbed fittings 126 (e.g., high pressure plastic fittings, metal fittings, etc.). Some braces 100 are implemented with other connection mechanisms. For example, the brace 100 illustrated in FIGS. 1A and 1B includes a manifold 116 extending vertically up the vest 110 to which each tube 112 is connected. In another example, some braces 100 have a single tube 112 that is wound in a serpentine fashion through multiple rib members 114. This approach reduces the need for connection fittings. The multiple tube approach can provide for easier replacement of portions of the system and can also make it easier to implement size-adjustable braces.

Figure 2A:
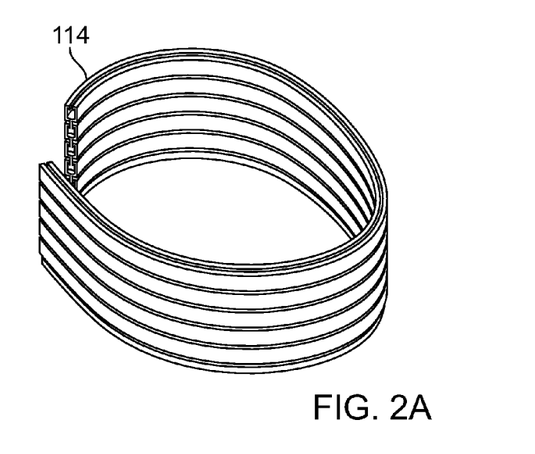
FIGS. 2A-2D are perspective views of inner components of a contour back brace.
Figure 2B:
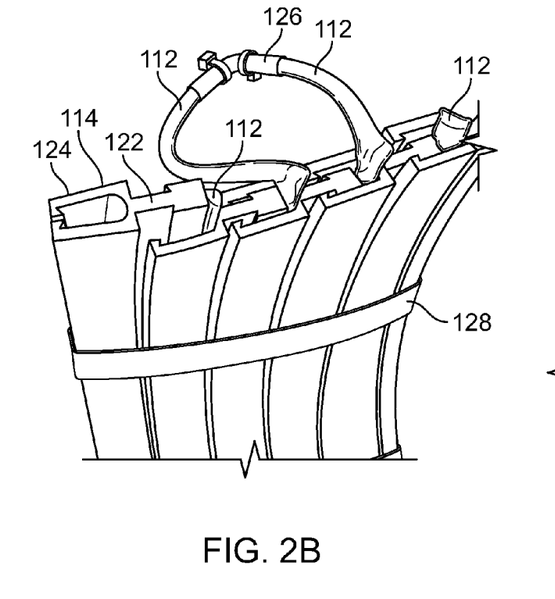
Figure 2C:
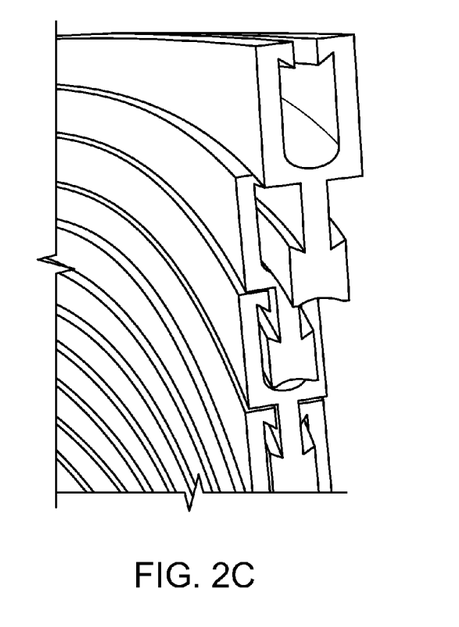
Figure 2D:
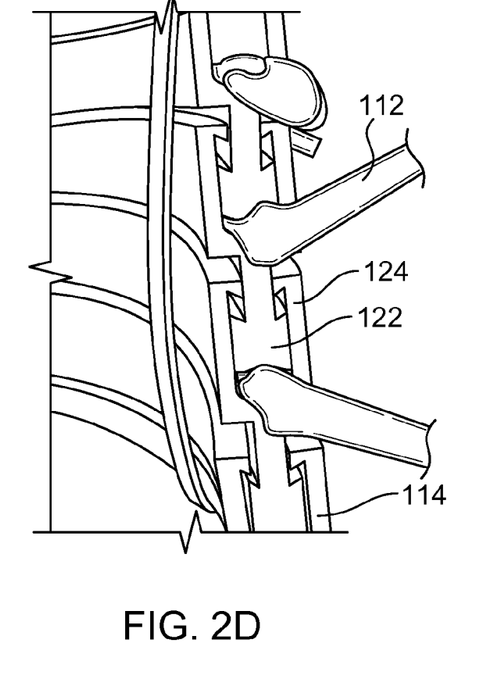
Figure 2E:
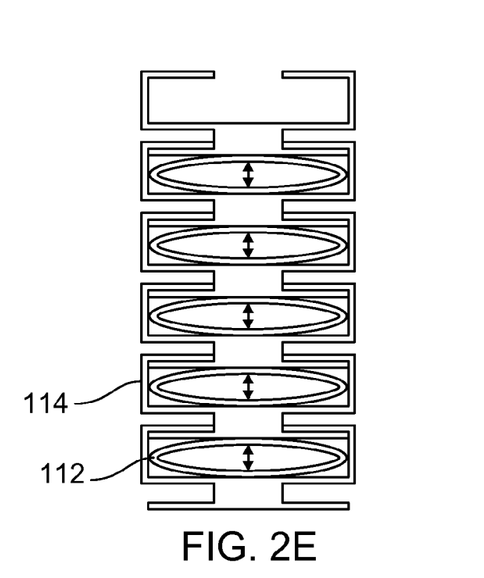
FIG. 2E is a schematic cross-section of a portion of the inner components of the contour back brace shown in FIG. 2A.

The entire garment system will be attached to the rib member/tubes in the prestretched state and can be coupled with a retraction mechanism 128 such as, for example, elastic bands 128 shown in see FIG. 2B. In some embodiments, the fabric of garment or brace covering can be an elastic material that acts as the retraction member. The retraction mechanism can provide a force biasing the rib members towards their collapsed neutral/"home" position when the tubes 112 are deflated as shown in FIG. 2B. In the collapsed position, these tubes, along with the interlocking rib member, can be further engineered to reduce overall size, therefore reducing the total system profile and appearance.

The contour brace for back mobilization therapy can provide a slight squeeze around the upper torso (depending on the hook and loop fastener, or buckle tensioning) and provide a straightening of the upper back for an aligned spine while lift takes place throughout the upper torso (e.g., throughout the entire upper torso) and spine establishing the proper upright posture and separation of the discs. The rib member and tubes can have various sizes (thickness, length and diameter) and be altered in location/position to accommodate the various upper torso shapes, weights and support requirements.

Figure 3:
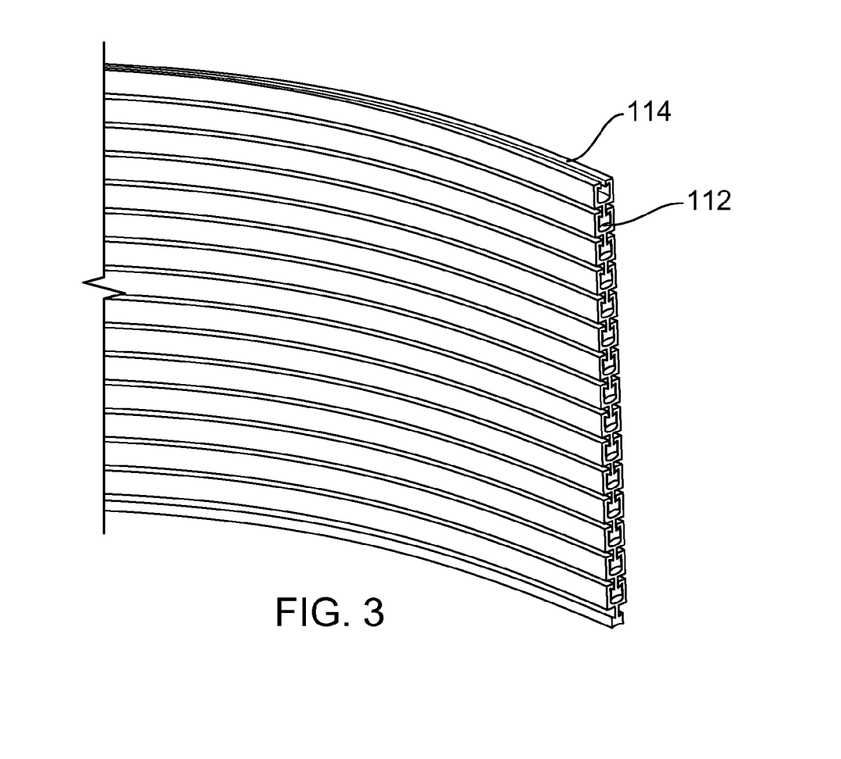
FIG. 3 is a perspective view of inner components of a contour back brace.
Figure 4:
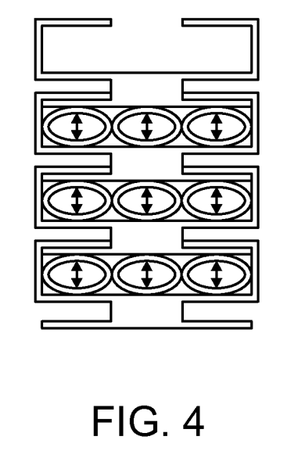
FIGS. 4 and 5 are schematic cross-sections of a portion of alternate embodiments of the inner components of the contour back brace shown in FIG. 2A.
Figure 5:
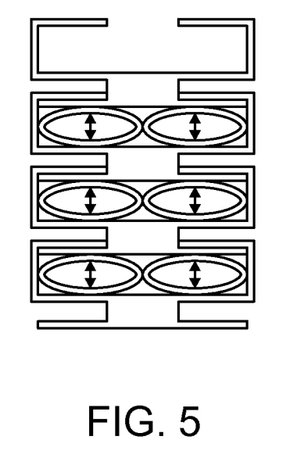

The brace 100 shown in FIGS. 2A-2E includes an inflatable tube 112 extending along the cavity defined between adjacent rib members. As shown in FIGS. 3 and 4, some braces 100 are implemented with multiple tubes 112 extending along the cavity defined between adjacent rib members 114. The multiple tube embodiments can provide more lifting force but can entail additional material and assembly costs relative to similar single tube embodiments.

FIG. 6 illustrates an embodiment of a rib member 114 that was used in a prototype contour back brace 100. The rib members 114 for the prototype were formed using the mold 130 shown in FIGS. 7A and 7B from a urethane material (within a specific mold as seen in FIG. 9, or can be extruded) of approximately 65 durometer. The rib members can also be formed using extrusion processes. Preliminary testing demonstrated the prototype brace 100 is capable of lifting 240 lbs. at 60 psi. The engineered rib member and tubes system is designed to provide substantial lift and support and can be adapted with embedded conductive materials to allow for hot and cold input fluid media to aid in back therapy.

In some embodiments (e.g., for a back brace), the height L of the rib member 114 can between 0.8 and 1.2 inches (e.g., approximately 1 inch). The height $L_1$ of the female end 124 of the rib member can be between 0.4 and 0.8 inches (e.g., approximately 0.56 inches). The height $L_2$ of the neck of the male end 122 of the rib member can be between 0.2 and 0.3 inches (e.g., approximately 0.26 inches). The height $L_3$ of the head of the male end 122 of the rib member can be between 0.15 and 0.25 inches (e.g., approximately 0.18 inches). The width W of the rib member can be between 0.35 and 0.4 inches (e.g., approximately 0.375 inches). The width $W_1$ of the head of the male end 122 of the rib member can be between 0.2 and 0.3 inches (e.g., approximately 0.2 inches). The width $W_2$ of the neck of the male end 122 of the rib member can be between 0.1 and 0.15 inches (e.g., approximately 0.125 inches). The dimensions of the rib members can differ from these ranges, particularly for other applications.

Figures 7A, 7B, 8:
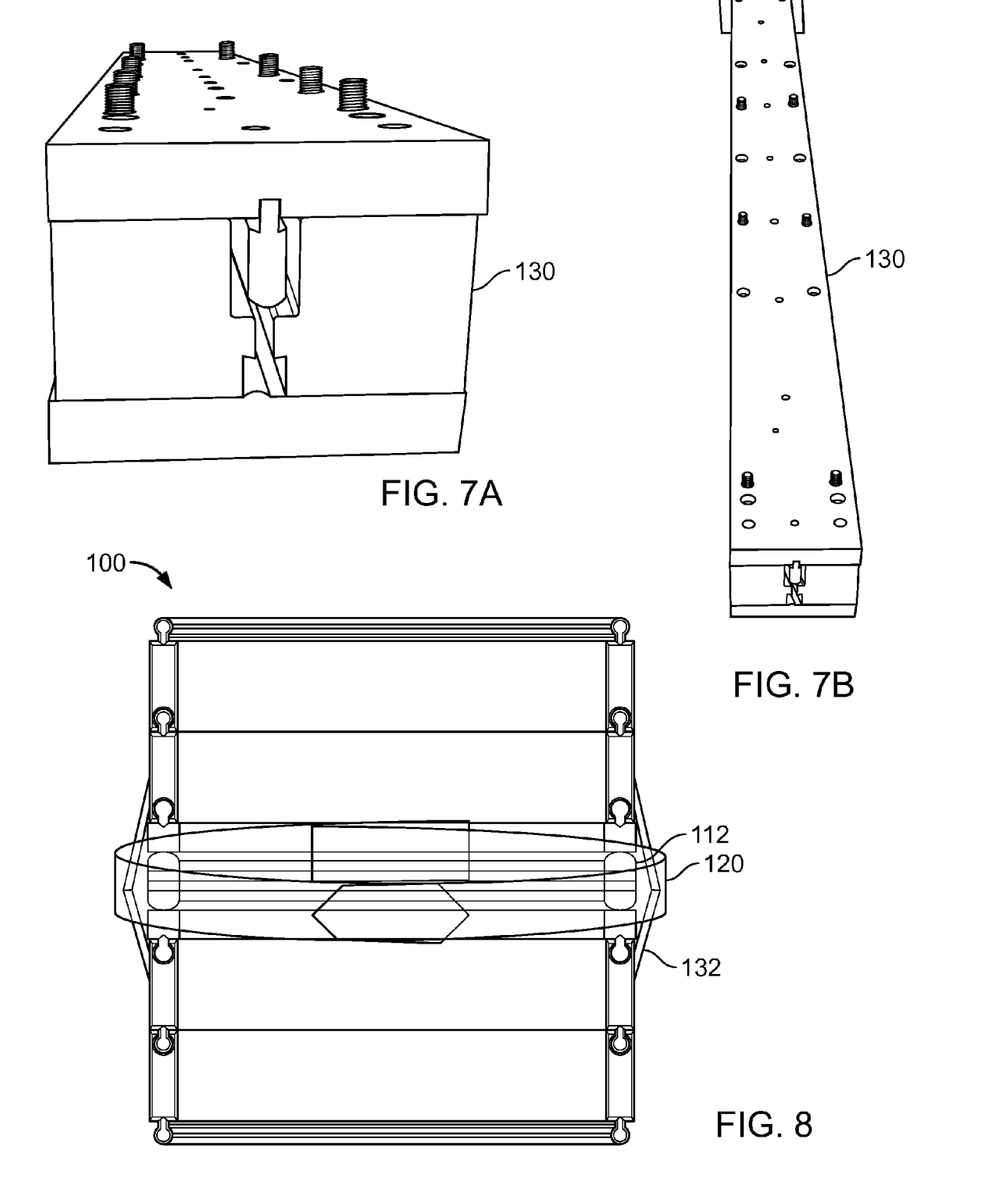
FIGS. 7A and 7B are perspective views of a mold used to form rib members.
FIG. 8 is a schematic illustration of a portion of a contour brace.

FIG. 8 schematic illustration of a portion of a contour brace 100 including an optional feature for non-pneumatic loading/preloading. The brace 100 includes a cam system 132 that is actuated via the cinching of the belt 120 (e.g., straps with Velcro hook and loop fasteners). The cam loading system 132 can be located at each belt location and is drawn inward as the belt 120 is tightened. Actuation of the cam system 132 can provide an incremental stretch of the rib member/tubes thereby creating a preloading condition making the overall system more efficient (e.g., less work to reach the final growth or expanded position). The cam system 132 can be incorporated into the contour braces for various physical applications including, for example, back braces, knee braces, etc.

Figures 9A, 9B:
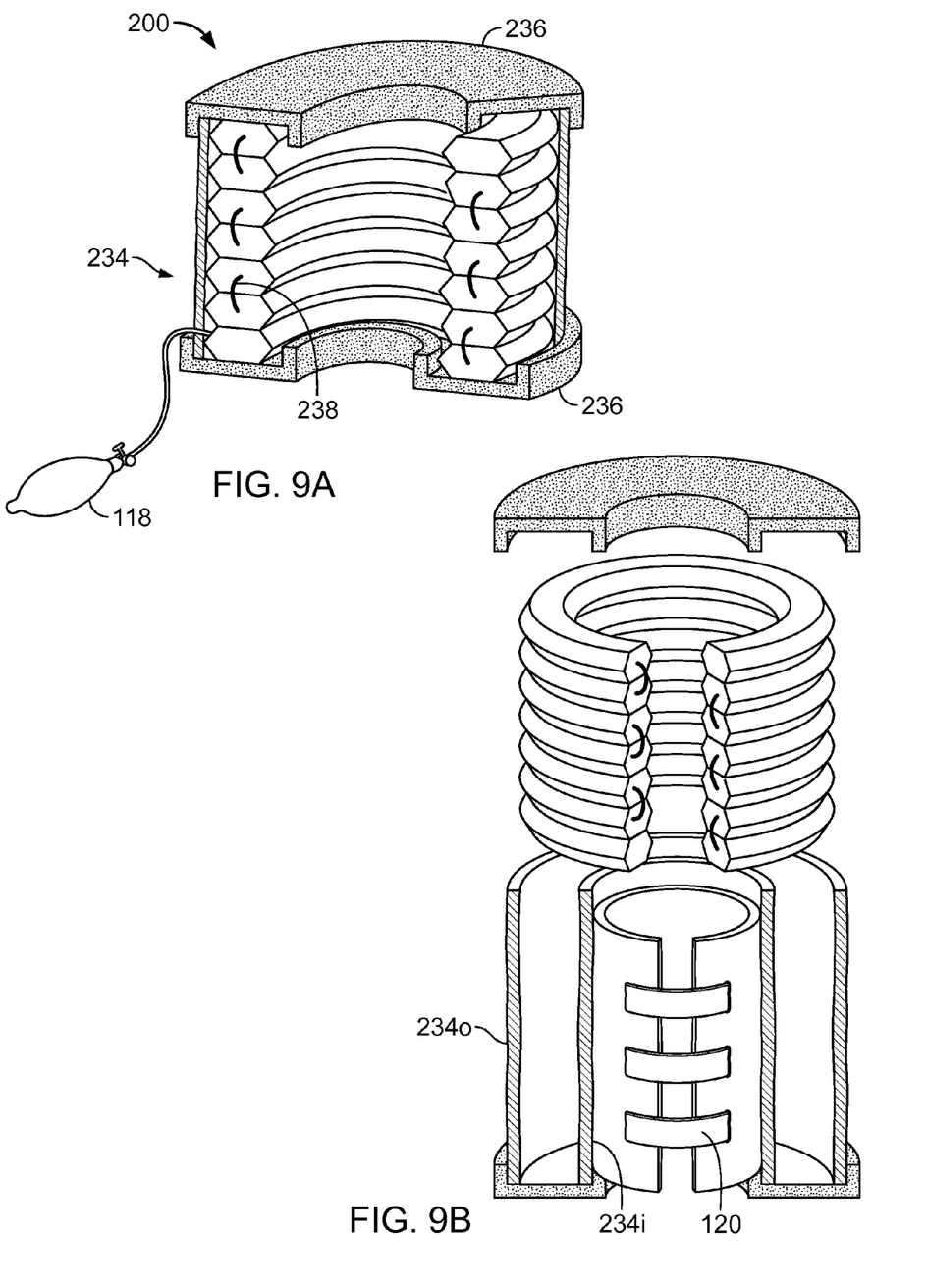
FIGS. 9A and 9B are partially cutaway perspective views of a neck contour brace.

FIGS. 9A and 9B are partially cutaway perspective views of a neck contour brace 200. The neck brace 200 includes inflatable tubes 112 disposed within a sleeve of textured material 234 with padded end caps 236. The illustrated brace 200 includes both an inner sleeve 234i and an outer sleeve 234o but some implementations include only the inner sleeve or only the outer sleeve. The brace 200 includes 7 stacked inflatable tubes connected by jumpers 238 for simultaneous inflation. The stacked arrangement of the tubes 112 can provide a vertical expansion of the brace 200 without significant radial expansion during inflation. This can provide tension to separate vertebrae in the neck without compressing the windpipe. Closure straps 120 are used to hold the neck brace 200 in position during inflation and use.

Figure 10:
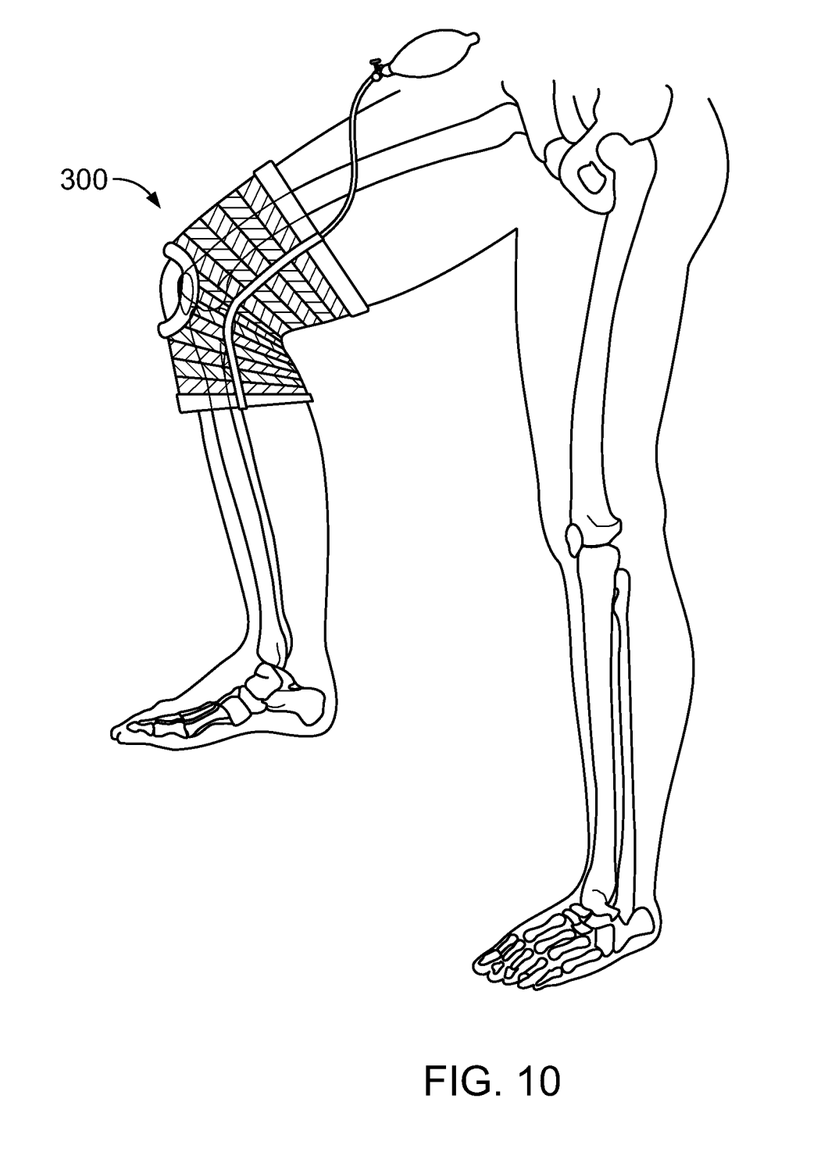
FIG. 10 is a schematic view of a knee contour brace.

FIG. 10 is a schematic view of a knee contour brace 300. The knee contour brace 300 is adapted to provide cushioning or compressional support for the knee. By wrapping the upper (femur) and lower (tibia/fibula) leg with the contour brace, inflation of the knee brace 300 can provide neutral positioning support without disturbing the ligaments. This would provide joint cushioning (dashpot) to reduce meniscus wear, arthritis, joint pain or pinching of nerves when walking, jogging, post-surgery, or ambulatory purposes.

The anterior cruciate ligament (ACL) is an important ligament for proper movement. ACL injury causes knee instability. Injuries of the ACL range from small tears to a completely torn ligament. The most common ACL tear is when the knee is bent too far towards the back and when it goes too far to the side. Tears in the anterior cruciate ligament occur when the knee receives a direct impact from the front of the thigh while the leg is in a stable position. Torn ACL's are often related to high impact sports or when the knee is forced to make sharp changes in movement and during abrupt stops from high speed. These types of injuries are prevalent in skiing, football, soccer, basketball, rugby, martial arts, and gymnastics. ACL tears can happen in older individuals through slips and falls and are seen in people over 40 due to wear and tear of the ligaments. An ACL tear can be determined by an individual if a popping sound is heard after impact, swelling after a couple of hours, severe pain when bending the knee, and when the knee buckles or locks during movement or gives way while standing still with weight on the affected knee. The knee contour brace 300 can provide support for damaged knees or help minimize or potentially prevent injury. In the case where ligament(s) is/are sensitive or damaged, the reversal of tubes in the knee contour brace 300 can provide a slight compressive force during inflation to deliver additional support to the knee and help compensate (or during rehabilitation) for a weak or damaged ACL.

The articular cartilage has limited capacity for self-repair and minor damage does not repair itself and can often get worse over time. As cartilage is a neural and avascular (lack of nerve and blood supply, respectively), shallow damage often does not trigger pain.

When the damage increases and the chondral defect reaches the subchondral bone, the blood supply in the bone starts a healing process in the defect. Scar tissue made up of a type of cartilage called fibrocartilage is then formed. Although fibrocartilage is able to fill in articular cartilage defects its structure is significantly different to that of hyaline cartilage; it is much denser and it doesn't withstand the demands of everyday activities as much as hyaline cartilage. It is therefore at a higher risk of breaking down.

Small articular cartilage defects can progress to osteoarthritis over time if left untreated. An articular cartilage defect that initially may be small still has the potential to have a physical and chemical "domino effect" on the surrounding "normal" articular cartilage. The knee contour brace 300 can either help reduce deterioration of an already damaged articular cartilage or mitigate by using in a preventive manner.

In some implementations, the cover of the knee brace 300 incorporates an interlocking weave around the upper thigh that tightens when pulled on. This feature coupled with high coefficient anti-slip material can help prevent brace slippage during use.

A number of embodiments of the invention have been described. Nevertheless, it will be understood that various modifications may be made without departing from the spirit and scope of the invention. Accordingly, other embodiments are within the scope of the following claims.

What is claimed is:

1. A wearable brace comprising:
   a plurality of elongated structural members disposed substantially in parallel with each other, each structural member engaged with at least one adjacent structural member; and
   at least one inflatable member disposed between two adjacent structural members such that inflation of the inflatable member biases portions of the two adjacent structural members away from each other;
   wherein each of the structural members has a male end and a female end sized such that the male end of one of the structural members can be inserted in slideable engagement into the female end of an adjacent structural member; and
   wherein the male end of each of the structural members comprises radially extending features that limit movement of two adjacent structural members away from each other after the male end of one of the structural members is inserted in slideable engagement into the female end of the adjacent structural member.

2. The wearable brace of claim 1, wherein the at least one inflatable member comprises one inflatable member disposed extending in a serpentine fashion between multiple sets of two adjacent structural members such that inflation of the one inflatable member biases portions of the two adjacent structural members in each set of two adjacent structural members away from each other.

3. The wearable brace of claim 1, wherein the at least one inflatable member comprises multiple inflatable members, each of the multiple inflatable members disposed between a different two adjacent structural members.

4. The wearable brace of claim 3, wherein each of the multiple inflatable members are fluidly connected to at least one other of the multiple inflatable members such the fluid used to fill the inflatable members extends in a serpentine fashion between multiple sets of two adjacent structural members.

5. The wearable brace of claim 3, further comprising a manifold connected to each of the multiple inflatable members.

6. The wearable brace of claim 1, further comprising a cover with the plurality of elongated structural members and the at least one inflatable member substantially disposed within the cover.

7. The wearable brace of claim 6, wherein the cover is configured to be worn on a torso of a user.

8. The wearable brace of claim 7, wherein the plurality of elongated structural members and the at least one inflatable member are sized to extend from hips of the user to armpits of the user.

9. The wearable brace of claim 6, wherein the cover is configured to be worn on a limb of a user.

10. The wearable brace of claim 9, wherein the cover is configured to be worn on a limb of a user.

11. The wearable brace of claim 10, wherein the cover is configured to be worn on a leg of a user.

12. The wearable brace of claim 1, further comprising a retraction mechanism biasing the plurality of elongated structural members towards a refracted position, the refraction mechanism configured to elastically expand when the plurality of elongated structural members are in an extended position.

13. The wearable brace of claim 12, wherein the retraction mechanism comprises an elastic band extending around multiple elongated structural members of the plurality of elongated structural members towards a retracted position.

14. The wearable brace of claim 12, wherein the retraction mechanism comprises a cover made of an elastic fabric with the plurality of elongated structural members and the at least one inflatable member substantially disposed within the cover.

15. A garment comprising:
    a plurality of elongated structural members disposed substantially in parallel with each other, each structural member engaged with at least one adjacent structural member, wherein each of the structural members has a male end and a female end sized such that the male end of one of the structural members can be inserted in slidable engagement into the female end of an adjacent structural member;
    at least one inflatable member disposed between two adjacent structural members such that inflation of the inflatable member biases portions of the two adjacent structural members away from each other; and
    a cover with the plurality of elongated structural members and the at least one inflatable member substantially disposed within the cover;
    wherein each of the structural members has a male end and a female end sized such that the male end of one of the structural members can be inserted in slideable engagement into the female end of an adjacent structural member; and
    wherein the male end of each of the structural members comprises radially extending features that limit movement of two adjacent structural members away from each other after the male end of one of the structural members is inserted in slideable engagement into the female end of the adjacent structural member.

16. The garment of claim 15, wherein the at least one inflatable member comprises multiple inflatable members, each of the multiple inflatable members disposed between a different two adjacent structural members.

17. The garment of claim 16, further comprising a manifold connected to each of the multiple inflatable members.

18. The garment of claim 15, further comprising a retraction mechanism biasing the plurality of elongated structural members towards a refracted position, the refraction mechanism configured to elastically expand when the plurality of elongated structural members are in an extended position.

* * * * *

UNITED STATES PATENT AND TRADEMARK OFFICE
CERTIFICATE OF CORRECTION

PATENT NO.         : 9,204,984 B2
APPLICATION NO.    : 13/907210
DATED              : December 8, 2015
INVENTOR(S)        : Robert Brown and Mario Santos Page 1 of 1

It is certified that error appears in the above-identified patent and that said Letters Patent is hereby corrected as shown below:

Claims

Claim 12

Column 12, line 9, delete "refracted" and insert -- retracted --.

Column 12, line 9, delete "refraction" and insert -- retraction --.

Claim 18

Column 12, line 56, delete "refracted" and insert -- retracted --.

Column 12, line 56, delete "refraction" and insert -- retraction --.

Signed and Sealed this
Fifth Day of July, 2016

Michelle K. Lee
*Director of the United States Patent and Trademark Office*